(12) United States Patent
Reimer et al.

(10) Patent No.: US 10,440,256 B2
(45) Date of Patent: Oct. 8, 2019

(54) SURGICAL MICROSCOPE AND METHOD IMPLEMENTED WITH THE SURGICAL MICROSCOPE

(71) Applicant: Carl Zeiss Meditec AG, Jena (DE)

(72) Inventors: Peter Reimer, Ellwangen (DE); Christian Beder, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 16/174,086

(22) Filed: Oct. 29, 2018

(65) Prior Publication Data

US 2019/0132526 A1 May 2, 2019

(30) Foreign Application Priority Data

Oct. 30, 2017 (DE) .................. 10 2017 125 453

(51) Int. Cl.
*H04N 5/232* (2006.01)
*A61B 3/13* (2006.01)
*A61B 3/10* (2006.01)
*A61B 3/14* (2006.01)
*G02B 27/00* (2006.01)
(Continued)

(52) U.S. Cl.
CPC ..... *H04N 5/232125* (2018.08); *A61B 3/1015* (2013.01); *A61B 3/13* (2013.01); *A61B 3/145* (2013.01); *G02B 21/0012* (2013.01); *G02B 27/0075* (2013.01); *A61B 90/20* (2016.02); *A61B 90/361* (2016.02)

(58) Field of Classification Search
CPC .. H04N 5/232125; A61B 3/1015; A61B 3/13; A61B 3/145; A61B 90/20; A61B 90/361
USPC .......................................................... 348/78
See application file for complete search history.

(56) References Cited

U.S. PATENT DOCUMENTS

| 7,031,054 B2 | 4/2006 | Cathey, Jr. et al. |
| 7,209,293 B2 | 4/2007 | Gaida et al. |
| 2010/0231713 A1* | 9/2010 | Oyabu ............... G01B 11/0608 348/143 |

FOREIGN PATENT DOCUMENTS

| DE | 103 38 472 A1 | 3/2005 |
| WO | 2006/102201 A1 | 9/2006 |

OTHER PUBLICATIONS

Sherif et al. "Reduced Depth of Field in Incoherent Hybrid Imaging Systems," Applied Optics, vol. 41, No. 29, pp. 6062 to 6074, Oct. 10, 2002.

(Continued)

*Primary Examiner* — Hee-Yong Kim
(74) *Attorney, Agent, or Firm* — Ewers & Hasselmann PLLC

(57) ABSTRACT

A surgical microscope, in particular an ophthalmic surgical microscope, includes a microscope imaging optical unit for imaging an object to be observed in an image plane along an optical imaging beam path, which passes through the microscope imaging optical unit, and a camera, which captures imaging of the object in the image plane. Further, the surgical microscope includes an optical wavefront encoding element that is positioned or positionable in the optical imaging beam path to influence an imaging light wavefront in the optical imaging beam path in such a way that a depth of field of the imaging of the object through the microscope imaging optical unit with the wavefront encoding element is reduced in relation to the depth of field of the imaging of the object through the microscope imaging optical unit without the wavefront encoding element.

13 Claims, 2 Drawing Sheets

(51) Int. Cl.
*G02B 21/00* (2006.01)
*A61B 90/20* (2016.01)
*A61B 90/00* (2016.01)

(56) References Cited

OTHER PUBLICATIONS

Office action by the German Patent and Trademark Office in 10 2017 125 453.6, which is a counterpart of this application, dated Jun. 20, 2018, along with the English-language translation thereof.

* cited by examiner

SURGICAL MICROSCOPE AND METHOD IMPLEMENTED WITH THE SURGICAL MICROSCOPE

CROSS REFERENCE TO RELATED APPLICATIONS

The present application claims priority to German patent application No. 10 2017 125 453.6 filed on Oct. 30, 2017, the entire content of which is incorporated in the present application by reference.

TECHNICAL FIELD

The disclosure relates to a surgical microscope, in particular an ophthalmic surgical microscope, comprising a microscope imaging optical unit that is configured to image an object to be observed into an image plane along an optical imaging beam path, which passes through the microscope imaging optical unit, and comprising a camera, which captures imaging of the object in the image plane.

Moreover, the disclosure relates to a method for measuring an object using a surgical microscope, in particular an ophthalmic surgical microscope, which comprises a microscope imaging optical unit that is configured to image the object to be observed into an image plane along an optical imaging beam path, which passes through the microscope imaging optical unit, wherein imaging of the object in the image plane is captured by a camera.

A surgical microscope according to the disclosure can be a monocular, a binocular or a stereoscopic surgical microscope.

BACKGROUND

By way of example, a surgical microscope of the type set forth at the outset is used in microsurgery. More specifically, such a surgical microscope can be used in ophthalmic surgery. Within this scope, cataract surgery has become particularly important. A "cataract" is understood to mean the opacification of the natural lens of the eye. In German, this disease is also known as "Grauer Star." Within the scope of cataract surgery, the opacified, natural lens of the eye is removed from the eye and replaced by an artificial lens for the eye, a so-called intraocular lens. Consequently, an "object" within the meaning of the present disclosure can be an eye of a patient, a specific structure of an eye, for example the cornea, more specifically the vertex of the front side of the cornea, to mention but a few examples.

The cataract surgery is usually carried out by a physician while observing the eye of the patient through an ophthalmic surgical microscope. Within the scope of the cataract operation, a refraction measurement is taken on the phakic, aphakic and/or pseudo-phakic eye. The state of the eye in which the natural lens is present in the eye is understood to be "phakic," the state in which the natural lens has been removed from the eye and the eye is without lens is understood to be "aphakic," and "pseudo-phakic" denotes the state in which an artificial lens has been inserted into the eye, wherein the artificial lens may be a temporary lens. The aforementioned refraction measurement comprises a distance measurement between the surgical microscope and the apex of the cornea of the eye, which must be carried out with high accuracy.

By way of example, to be able to measure an aphakic patient's eye with the required measurement accuracy with a wavefront-based intraoperative refraction measurement, the measurement distance must be known, or maintained, within an accuracy range of 0.3 mm.

In general, when using surgical microscopes in certain applications in microsurgery, it is necessary to establish the distance between the surgical microscope and the observed object accurately, which assumes that the object-side focal plane of the surgical microscope is set exactly to the object to be measured.

These days, this setting is realized by the use of autofocus systems, for example, with which surgical microscopes may be equipped. Such autofocus systems can be based on a contrast evaluation of a camera image. To this end, such a surgical microscope comprises a camera which captures the image representation of the object in the image plane. Within the meaning of the present disclosure, a "camera" is understood to mean, in general, an image recorder or an image sensor. In particular, the camera can be a video camera.

The image recorded by the camera is evaluated in terms of the contrast thereof and the autofocus system adjusts the focal plane of the surgical microscope until the camera image of the object recorded by the camera has a maximum contrast. Here, the accuracy of the correct focal plane setting is determined, inter alia, by the depth of field of the imaging of the observed object onto the image plane, in which the camera is situated. Here, "depth of field" is understood to mean a distance range in front of and behind the object-side setting or focal plane, within which an object can be displaced axially without noticeable blurring of the imaging arising in the image plane.

In current surgical microscopes with an autofocus system, an accurate distance measurement cannot be realized, or can only be realized approximately, on account of the depth of field of the imaging that is too high, at least at magnifications of the surgical microscope at which a physician carries out the cataract surgery. By way of example, if the surgical microscope should be set exactly onto the vertex of the front side of the cornea for the purposes of measuring a distance, this cannot be brought about by the autofocus system on the basis of a contrast evaluation of the camera image since regions in front of and behind the vertex of the cornea appear in the camera image with the same high contrast.

On the other hand, it is desirable in principle for surgical microscopes to have a large depth of field because the tissue operated on by the physician does not, as a rule, form a plane but it is craggy instead. Therefore, attempts are always made to facilitate in-focus vision for all regions of an operating region. This is particularly important in the case of surgery on the eye since, by way of the cornea, the pupil and the lens, there are a plurality of transparent tissues that lie over one another.

Thus, U.S. Pat. No. 7,209,293 B2 proposes to further increase the depth of field of a surgical microscope by means of an optical phase-shift element in the imaging beam path of the microscope imaging optical unit. However, this is detrimental to accurately measuring a distance with the surgical microscope. A reduction in the depth of field in the case of autofocus systems for surgical microscopes can be obtained by increasing the aperture of the microscope imaging optical unit. However, this is disadvantageous in that the optical system of the surgical microscope becomes significantly larger overall, as larger free diameters of the microscope imaging optical unit are required.

The phase contrast method for reducing the depth of field is known from the field of digital cameras with a video function; however, the method requires specific image recorders which, for example, have a plurality of sensors in different planes.

SUMMARY

The disclosure is therefore based on the object of developing a surgical microscope of the type set forth at the outset in such a way that an object can be measured with a high accuracy using the surgical microscope.

In respect of the surgical microscope specified at the outset, this object is achieved by virtue of the surgical microscope comprising an optical wavefront encoding element that is positioned or positionable in the optical imaging beam path and embodied to influence an imaging light wavefront in the optical imaging beam path in such a way that a depth of field of the image of the object through the microscope imaging optical unit with the wavefront encoding element is reduced in relation to a depth of field of the image of the object through the microscope imaging optical unit without the wavefront encoding element.

Consequently, the surgical microscope according to the disclosure is based on the concept of reducing the depth of field of the image through the microscope imaging optical unit with a wavefront encoding element, which is typically introduced only on a temporary basis, into the imaging beam path, in particular for the purposes of measuring an object, more particularly for measuring the distance between the surgical microscope and an object. The wavefront encoding element, which may be a phase-shifting element, for example, can be configured to be suitable to this end. The wavefront encoding element is an optical element that, when arranged in the imaging beam path, changes the optical transfer function of the microscope imaging optical unit in such a way that the imaging has a stronger variance or dependence of the offset of the object from the setting plane or focal plane of the surgical microscope. An example of a wavefront encoding element that can be used to reduce the depth of field is described in the article "Reduced Depth of Field in Incoherent Hybrid Imaging Systems" by Sherif S. Sherif and W. Thomas Cathey, Applied Optics, volume 41, number 29, 10 Oct. 2002, pages 6062 to 6074. When the wavefront encoding element is arranged in the imaging beam path of the surgical microscope, it is consequently possible to accurately establish distances between the surgical microscope and objects to be measured, or the object-side setting plane or focal plane of the surgical microscope can be set onto the object to be measured with a higher accuracy than previously.

The depth of field which is intended to be reduced in the surgical microscope according to the disclosure by means of the wavefront encoding element is the object-side depth of field.

Typically, the surgical microscope comprises a computer unit, which calculates an image with a reduced depth of field for further processing purposes from the image of the object with a reduced depth of field captured by the camera.

When the wavefront encoding element is arranged in the imaging beam path, the image through the microscope imaging optical unit overall is blurred; i.e., the camera captures a brightness distribution in the image plane with its image pixels. Then, from the brightness values of the camera image signals, the computer unit calculates an image which has a reduced depth of field, it then being possible to process the image further, for example by virtue of the image being displayed to the observer on a screen, following which the observer can focus the image by focusing the microscope imaging optical unit. If the microscope imaging optical unit comprises an autofocus system, as is provided in a typical configuration, the computer unit can evaluate the image with a reduced depth of field and can produce data that are used by the autofocus system for automatically focusing the image with a reduced depth of field. Once the image is in focus, the focal plane of the surgical microscope is set with high accuracy onto the object to be measured, and so the distance to the object can be established, or it is known, accurately.

Expressed differently, the autofocus system present in the surgical microscope can set the focal plane of the surgical microscope to a certain object plane with a substantially higher accuracy, as a result of which the distance measurement is substantially more accurate.

Typically, the wavefront encoding element is able to be introduced into the imaging beam path and able to be removed therefrom again.

What is advantageous here is that the depth of field of the imaging through the microscope imaging optical unit is not reduced permanently as this, as already mentioned above, is undesirable in surgical microscopes; instead, it is only reduced for the purposes of measuring objects.

Further typically, the wavefront encoding element is positioned or positionable at a point in the imaging beam path at which the imaging beam path is parallel, or the wavefront encoding element is positioned or positionable in a pupil plane in the imaging beam path.

Typically, the wavefront encoding element is a phase-shifting element. A "phase-shifting element" is a wavefront encoding element that is light-transmissive and that impresses a phase offset onto a light beam passing therethrough, the phase offset depending on the location of the passage of the light rays through the phase-shifting element.

Further typically, the depth of field of the imaging of the object through the microscope imaging optical unit into the image plane with the wavefront encoding element is reduced to a depth of field of less than 1 mm, typically less than 0.75 mm, more typically to a depth of field of approximately 0.3 mm.

Consequently, the surgical microscope according to the disclosure can be used to measure distances between the surgical microscope and the objects to be observed with an accuracy of less than 1 mm, typically approximately 0.3 mm. Consequently, the surgical microscope according to the disclosure is particularly suitable for a wavefront-based intraoperative refraction measurement of an aphakic patient's eye, whereby the measurement distance can be established with a measurement accuracy of approximately 0.3 mm.

The depth of field of the imaging of the object through the microscope imaging optical unit into the image plane with the wavefront encoding element is typically reduced by a factor in the range of 1.5 to 5 in relation to the depth of field of the image representation of the object through the microscope imaging optical unit without the wavefront encoding element.

Consequently, the surgical microscope according to the disclosure has a great depth of field, which facilitates the observation of uneven structures with great sharpness, when the wavefront encoding element is not arranged in the imaging beam path of the microscope imaging optical unit.

According to the disclosure, the method set forth at the outset includes the step of: reducing a depth of field of the image representation of the object by arranging an optical wavefront encoding element in the optical imaging beam path, the optical wavefront encoding element being embodied to influence an imaging light wavefront in the optical imaging beam path in such a way that the depth of field of the imaging of the object through the microscope imaging optical unit with the wavefront encoding element is reduced in relation to a depth of field of the imaging of the object through the microscope imaging optical unit without the wavefront encoding element.

The aforementioned preferred configurations of the surgical microscope according to the disclosure can also be used in the method according to the disclosure. Likewise, the method according to the disclosure has the advantages as were, and still will be, described in relation to the surgical microscope according to the disclosure.

It goes without saying that the aforementioned features and those yet to be explained below may be used not only in the respectively specified combination but also in other combinations or on their own, without departing from the scope of the present disclosure.

BRIEF DESCRIPTION OF THE DRAWINGS

The disclosure will now be described with reference to the drawings wherein:

FIG. 1 shows a surgical microscope that has been provided with the general reference sign 10. In particular, the surgical microscope 10 is an ophthalmic surgical microscope that is used in eye surgery. Here, the surgical microscope 10 is shown as a monocular surgical microscope, with it being understood that a surgical microscope according to the disclosure can also be embodied as a binocular surgical microscope or as a stereoscopic surgical microscope.

Figure 1:
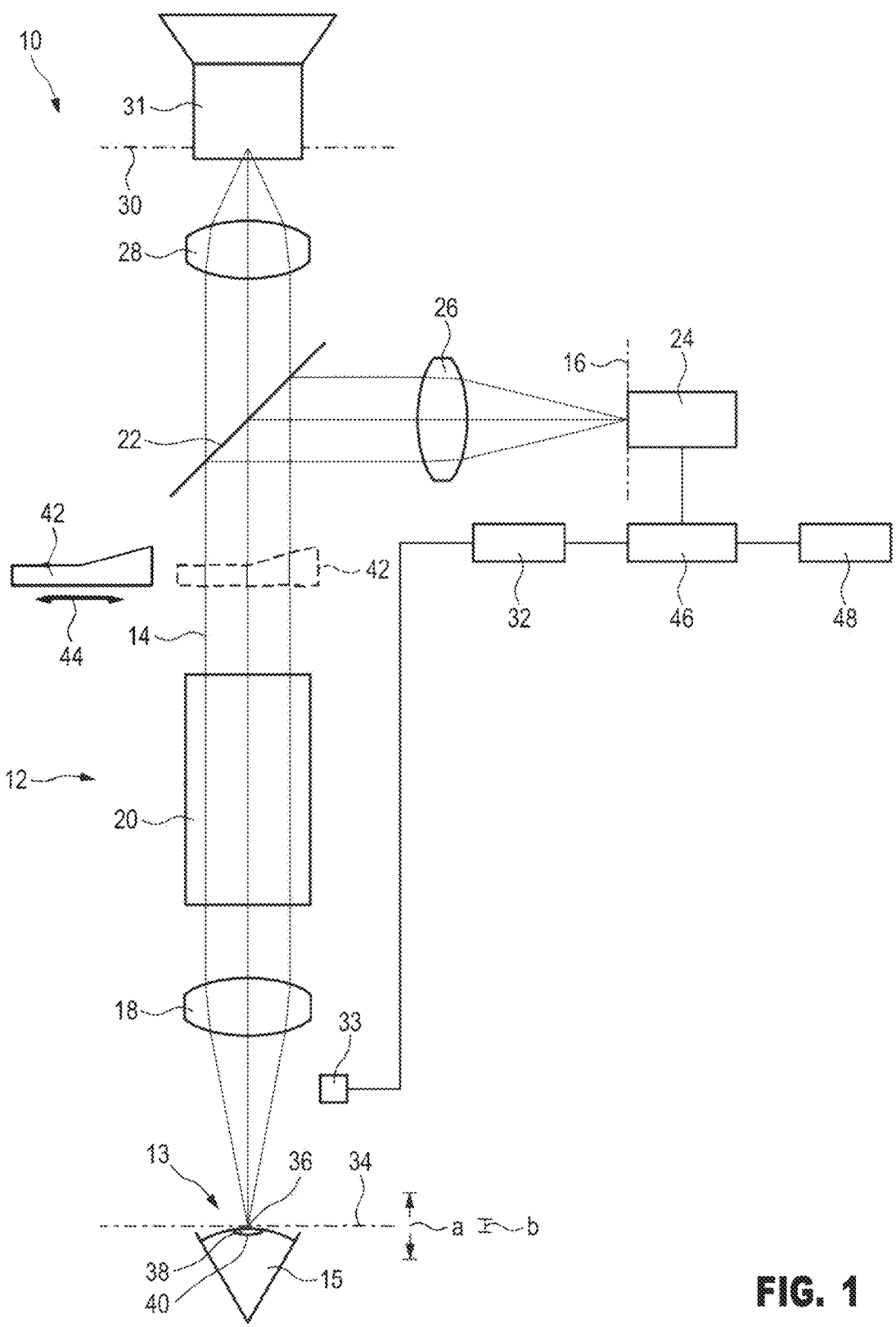
FIG. 1 shows a surgical microscope in a schematic side view.

The surgical microscope 10 comprises a microscope imaging optical unit 12 that is configured to image an object 13 to be examined into an image plane 16 along an optical imaging beam path 14, which passes through the microscope imaging optical unit 12. Here, the object 13 is an eye 15 of a patient or a part, for example a surface, of the eye.

In FIG. 1, the optical units of the microscope imaging optical unit 12 are only shown schematically and, moreover, not true to scale.

The microscope imaging optical unit 12 comprises a main objective 18. Furthermore, the microscope imaging optical unit 12 may comprise a zoom system 20, by means of which it is possible to set different magnifications of the imaging by the surgical microscope 10.

Part of the imaging beam path 14 is guided to a camera 24, in particular a video camera, via a beam splitter 22. A camera optical unit 26 can be arranged between the beam splitter 22 and the camera 24, the camera optical unit focusing the imaging beam path 14 onto the image plane 16, with an image sensor of the camera 24 being arranged in the image plane 16. The camera optical unit 26 can be part of the camera 24 or else be a separate optical unit. The camera 24 may also comprise only the image sensor. The camera 24 captures the object 13 imaged in the image plane 16.

Another part of the imaging beam path 14 passes through the beam splitter 22 and is imaged by a tubular optical unit 28 into an eyepiece-side image plane 30. With their eye, the user of the surgical microscope 10 can observe this image of the object 13 by means of an eyepiece 31.

The surgical microscope 10 is equipped with an autofocus system 32, wherein the camera 24 may be part of the autofocus system 32. With the autofocus system 32, it is possible to set the object-side focal plane 34 of the microscope imaging optical unit 12 of the surgical microscope 10 onto the object 13, in particular for the purposes of measuring the object 13. To this end, FIG. 1 schematically shows an adjustment unit 33, to which the autofocus system 32 is connected. The adjustment unit 33 can be embodied in such a way that it can displace the surgical microscope 10 as a whole toward the focal plane 34, or away from the latter, or the adjustment unit 33 can be embodied in such a way that it correspondingly adjusts the main objective 18 in the case where the main objective 18 is adjustable in terms of its focal length. By way of example, for the purpose of setting the focal plane 34 onto the object 13, the autofocus system 32 uses a contrast evaluation of the image of the object 13, as recorded by the camera 24. The autofocus system evaluates that object-side plane which supplies the strongest contrast in the image of the camera 24 as being the focal plane 34 of the microscope imaging optical unit 12. However, the evaluation of the contrast is inaccurate if the microscope imaging optical unit 12 images the object 13 with a large object-side depth of field into the image plane 16.

Here, the object-side depth of field is understood to mean a distance range a in front of and behind the setting or focal plane 34 of the microscope imaging optical unit 12, within which the object 13 can be displaced axially without noticeable blurring of the imaging arising in the image plane 16.

On account of a depth of field being too large, the autofocus system 32 is unable to set the surgical microscope 10 onto the focal plane or setting plane 34, in which the object 13 to be measured is arranged, with sufficient accuracy. By way of example, if the distance between the surgical microscope and the apex 36 of the cornea 38 of the eye 15 should be measured in the case of a reflection measurement within the scope of cataract surgery, the surgical microscope 10 must be focused or set on the apex 36 of the cornea 38 with a high accuracy. On account of the depth of field (distance range a), however, this is not possible with sufficient accuracy as the autofocus system 32, which is based on a contrast evaluation, cannot discriminate between the respective setting planes with sufficient accuracy because planes at a comparatively large distance range a in front of and behind the setting plane are also imaged with a high contrast, i.e., with great sharpness, into the image plane 16.

To reduce the object-side depth of field, a wavefront encoding element 42 is provided in the surgical microscope 10. When the wavefront encoding element 42 is introduced into the imaging beam path 14, the encoding element 42 influences the imaging light wavefront in the optical imaging beam path 14 in such a way that, as illustrated by the dashed lines in FIG. 1, the object-side depth of field of the imaging of the object 13 through the microscope imaging optical unit 12 is reduced in relation to the object-side depth of field of the imaging of the object 13 through the microscope imaging optical unit without the wavefront encoding element 42, as indicated by a reduced distance range b in FIG. 1. In an exemplary embodiment, the distance range b is close to zero. The wavefront encoding element is an optical element that, when arranged in the imaging beam path, changes the optical transfer function of the microscope imaging optical unit in such a way that the imaging has a stronger variance or dependence on the offset of the object from the setting plane or focal plane of the surgical microscope.

The wavefront encoding element 42 is only shown schematically in FIG. 1.

Figure 2:
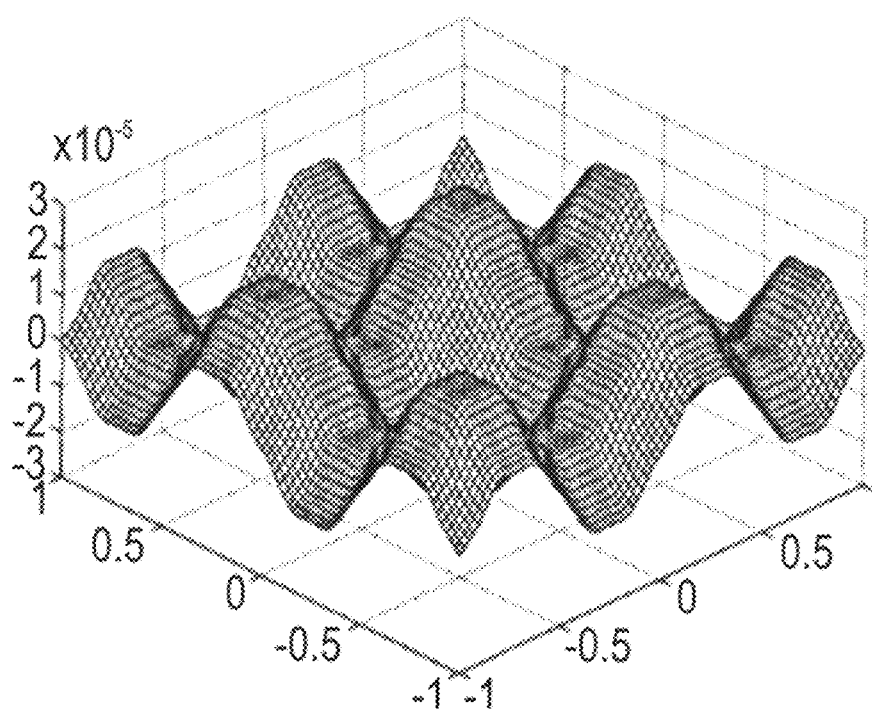
FIG. 2 shows a diagram which elucidates an exemplary surface profile of a wavefront encoding element for reducing the depth of field of the imaging by the surgical microscope.

The wavefront encoding element 42 can be configured as a phase-shifting element. The phase-shifting element is a light-transmissive optical element that impresses a phase offset onto a light beam passing therethrough, the phase offset depending on the location of the passage of the light rays through the phase-shifting element. FIG. 2 shows an exemplary embodiment of a surface profile of a phase-shifting element, by means of which the depth of field of the imaging of the object 13 can be reduced in relation to the depth of field without the wavefront encoding element 42. A phase-shifting element of this type is described in the article to Sherif et al. discussed in paragraph [0018] above, which is incorporated herein by reference in its entirety.

A suitable phase-shifting element can satisfy the function $f(x,y)=\cos(\beta\pi x)\cos(\beta\pi y)$ in the xy-plane, where $\beta$ is a constant.

The wavefront encoding element 42 is able to be introduced into the imaging beam path 14 and able to be removed from the imaging beam path 14 again, as per double-headed arrow 44. The wavefront encoding element 42 is introduced into the imaging beam path 14 when measuring the object 13 and can be removed from the imaging beam path 14 for the purpose of observing the object 13 with a large depth of field.

The object 13 is imaged into the image plane 16 with a reduced object-side depth of field when the wavefront encoding element 42 is arranged in the imaging beam path 14. However, as a general rule, imaging in the image plane 16 will be out of focus overall; i.e., even an object (e.g., the front side of the cornea 38) in the setting or focal plane 34 of the microscope imaging optical unit 12 is not imaged in focus into the image plane 16. Therefore, provision is made of a computer unit 46, which calculates an image with a reduced depth of field for further processing from the imaging of the object 13 with a reduced depth of field captured by the camera 24 in the image plane 16. This calculated image can be displayed on a rendering unit 48, for example a screen. The user of the surgical microscope 10 can then focus the surgical microscope 10 manually until the image displayed by the image rendering unit 48 is in focus.

In addition or as an alternative thereto, the computer unit 46 can evaluate the calculated image with a reduced depth of field and can produce data that are supplied to the autofocus system 32 for automatically focusing the image with reduced depth of field. The in-focus image is now the image of the object which lies in, or at least very close to, the setting or focal plane 34.

In the shown exemplary embodiment, the wavefront encoding element is positioned or positionable at a point in the imaging beam path 14 at which the imaging beam path 14 is parallel. In the surgical microscope 10, the imaging beam path 14 is parallel at the output-side of the zoom system 20, and so the wavefront encoding element 42 can advantageously be positioned between the zoom system 20 and the beam splitter 22. The wavefront encoding element 42 can also be positioned in a pupil plane in the imaging beam path 14. A further option for positioning the wavefront encoding element 42 exists at a position between the beam splitter 22 and the camera optical unit 26, typically in, or near to, a plane that is conjugate to the pupil plane of the imaging beam path 14.

The wavefront encoding element 42 can be configured in such a way that the object-side depth of field of the imaging of the object 13 through the microscope imaging optical unit 12 into the image plane 16 with the wavefront encoding element 42 is reduced to a depth of field (distance range b) of less than 1 mm, or even to a depth of field of approximately 0.3 mm.

The wavefront encoding element 42 can be configured to reduce the depth of field in relation to the depth of field without the wavefront encoding element 42 by a factor in the range of 1.5 to 5.

In a method for measuring an object to be observed, the wavefront encoding element 42 is introduced into the imaging beam path 14, as described above. The wavefront encoding element 42 reduces the depth of field of the image of the object 13 in the image plane 16.

The method for measuring the object 13 can be, for example, refraction measurement on the phakic, aphakic, or pseudo-phakic eye 15.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A surgical microscope comprising:
   a microscope imaging optical unit configured to image an object to be examined in an image plane along an optical imaging beam path passing through the microscope imaging optical unit;
   a camera configured to capture an image of the object in the image plane;
   an optical wavefront encoding element that is positioned or positionable in the optical imaging beam path, wherein the optical wavefront encoding element is configured to influence an imaging light wavefront in the optical imaging beam path, wherein the microscope imaging optical unit images the object to be examined in the image plane with a depth of field when the optical wavefront encoding element is not positioned in the optical imaging beam path, and wherein the microscope imaging optical unit images the object to be examined in the image plane with a reduced depth of field when the optical wavefront encoding element is positioned in the optical imaging beam path;
   a computer unit configured to calculate an image with the reduced depth of field for further processing from an image of the object with the reduced depth of field captured by the camera; and
   an autofocus system configured to receive data from the computer unit to automatically focus the image of the object with the reduced depth of field.

2. The surgical microscope according to claim 1, further comprising:
   an image rendering unit configured to display at least one of the image of the object with the depth of field or the image of the object with the reduced depth of field on a screen.

3. The surgical microscope according to claim 1, wherein the optical wavefront encoding element can be brought into the optical imaging beam path and to be subsequently removed from the optical imaging beam path.

4. The surgical microscope according to claim 1, wherein the optical wavefront encoding element is positioned or positionable at a point in the optical imaging beam path at which the optical imaging beam path is parallel; or the optical wavefront encoding element is positioned or positionable in, or in the vicinity of, a pupil plane; or the optical wavefront encoding element is positioned or positionable in, or in the vicinity of, a plane conjugate to the pupil plane in the optical imaging beam path.

5. The surgical microscope according to claim 1, wherein the microscope imaging optical unit further comprises:
   a zoom system, wherein the optical imaging beam path is parallel on an output-side of the zoom system, and wherein the optical wavefront encoding element is positioned or positionable downstream of the zoom system, as seen in a direction of the optical imaging beam path.

6. The surgical microscope according to claim 1, wherein the optical wavefront encoding element is a phase-shifting element.

7. The surgical microscope according to claim 1, wherein the reduced depth of field is less than 1 mm.

8. The surgical microscope according to claim 1, wherein the reduced depth of field is reduced by a factor in a range of from 1.5 to 5 in relation to the depth of field.

9. A method for measuring an object with a surgical microscope, the method comprising:
   providing a surgical microscope including:
      a microscope imaging optical unit configured to image an object to be examined in an image plane along an optical imaging beam path passing through the microscope imaging optical unit;
      a camera configured to capture an image of the object in the image plane;
      an optical wavefront encoding element that is positioned or positionable in the optical imaging beam path;
      a computer unit configured to calculate an image with a reduced depth of field for further processing from an image of the object with the reduced depth of field captured by the camera; and
      an autofocus system configured to receive data from the computer unit to automatically focus the image with the reduced depth of field;
   arranging an object to be examined on an object side of the microscope imaging optical unit;
   positioning the optical wavefront encoding element in the optical imaging beam path;
   imaging the object to be examined in the image plane;
   capturing an image with a reduced depth of field of the object to be examined with the camera for further processing; and
   automatically focusing the image with the reduced depth of field of the object to be examined.

10. The surgical microscope according to claim 1, wherein the surgical microscope is an ophthalmic surgical microscope.

11. The surgical microscope according to claim 1, wherein the reduced depth of field is less than 0.75 mm.

12. The surgical microscope according to claim 1, wherein the reduced depth of field is approximately 0.3 mm.

13. The method according to claim 9, wherein the surgical microscope is an ophthalmic surgical microscope.

* * * * *